United States Patent [19]

Steiner et al.

[11] Patent Number: 5,503,852

[45] Date of Patent: *Apr. 2, 1996

[54] METHOD FOR MAKING SELF-ASSEMBLING DIKETOPIPERAZINE DRUG DELIVERY SYSTEM

[75] Inventors: Solomon S. Steiner, Mount Kisco, N.Y.; Christopher A. Rhodes, Stamford, Conn.; Gregory S. Shen, Hartsdale, N.Y.; R. Tyler McCabe, Yorktown, N.Y.

[73] Assignee: Pharmaceutical Discovery Corporation, Elmsford, N.Y.

[ * ] Notice: This term of this patent shall not extend beyond the expiration date of Pat. No. 5,352,461.

[21] Appl. No.: 299,842

[22] Filed: Sep. 1, 1994

Related U.S. Application Data

[63] Continuation-in-part of Ser. No. 849,186, Mar. 11, 1992, Pat. No. 5,352,461.

[51] Int. Cl.[6] ............................... A61K 9/16; A61K 9/50
[52] U.S. Cl. ........................... 424/493; 424/489; 424/490
[58] Field of Search .................................. 424/493, 489, 424/490

[56] References Cited

U.S. PATENT DOCUMENTS

| 4,925,673 | 5/1990 | Steiner et al. | 424/455 |
|---|---|---|---|
| 4,976,968 | 11/1990 | Steiner | 424/491 |
| 4,983,402 | 1/1991 | Steiner | 424/491 |
| 5,352,461 | 10/1994 | Feldstein et al. | 424/493 |

FOREIGN PATENT DOCUMENTS

| 0284039 | 9/1988 | European Pat. Off. . |
|---|---|---|
| 0333523 | 9/1989 | European Pat. Off. . |
| 0350246A2 | 1/1990 | European Pat. Off. . |
| 0350246 | 1/1992 | European Pat. Off. . |
| 2145555 | 2/1973 | France . |
| 1155036 | 6/1969 | United Kingdom . |
| 1255805 | 12/1971 | United Kingdom . |

WO91/06287 5/1991 WIPO .

OTHER PUBLICATIONS

Fox, S., "A New View of the 'Synthesis of Life'", *Quarterly Journal of the Florida Academy of Sciences*, 31, 1968, 1–15.

Fox, S., "A theory of macromolecular and cellular origins", *Nature*, 205, 1965, 328–340.

Fox, S., "How did life begin?", *Science & Technology*, Feb. 1968, 51–61.

Fox, S., et al., "Fractionation and characterization of an amidated thermal I:I:I–proteinoid", *Biochimica et Biophysica Acta*. 140, 1967, 155–167.

Fox, S. W., et al., "Thermal Polymerization of Amino Acids and a Theory of Biochemical Origins," *Experientia* vol. XV:81–84 (1959).

Fusaoka, Y., et al., "Synthesis and interaction with metal ions of cyclic oligopeptides bearing carboxyl groups", *International Journal of Peptide & Protein Research*, 34, 1989, 104–110.

Ghadiri, M., et al., "Self-assembling organic nanotubes based on a cyclic peptide architecture", *Nature* 336, 1993, 324–327.

(List continued on next page.)

*Primary Examiner*—Thurman K. Page
*Assistant Examiner*—William E. Benston, Jr.
*Attorney, Agent, or Firm*—Arnall Golden & Gregory

[57] ABSTRACT

Drug delivery systems have been developed based on the formation of diketopiperazine (or analogs) microparticles. In the preferred embodiment the microparticle is stable at low pH and disintegrates at physiological pH, and is particularly useful for oral drug delivery. In other embodiments, the microparticles are stable at high pH and disintegrate at neutral or basic pH, or are stable at neutral pH and disintegrate at high or low pH. In the most preferred embodiment the microparticles are formed in the presence of the drug to be delivered, for example, insulin, felbamate, calcitonin or heparin. The diketopiperazine synthetic intermediates are preferably formed by cyclodimerization to form diketopiperazine derivatives at elevated temperatures under dehydrating conditions, functionalized on the side chains, and then precipitated with drug to be incorporated into microparticles.

28 Claims, 5 Drawing Sheets

OTHER PUBLICATIONS

Györe, J., and M. Ecet, "Thermal Behaviour of Phenylalanine and Aminophenylalanine", *Thermal Analysis* vol. 2–Proceedings fourth ICTA, Budapest, pp. 387–394 (1974).

Lannom, H., et al., "$^{13}$C n.m.r. study of the structure and the metal ion binding sites of neuropeptides composed of L–Asp and L–Glu", *Int. J. Peptide Protein Res.* 28, 1986, 67–78.

Mazurov, A., et al., "Formation of pyroglutamylglutamine (or asparagine) diketopiperazine in 'non–classical' conditions: a side reaction in peptide synthesis", *Int. J. Peptide Protein Res.* 42, 1993, 14–19.

Ogura, H., et al., "Studies on Lactams, VI. Stereochemistry of L–Prolyl–L–valine Anhydride", *Chemical & Pharmaceutical Bulletin*, 23, 1975, 2474–2477.

Perlstein, J., "Molecular Self–Assemblies 2. A Computational Method for the Prediction of the Structure of One–Dimensional Screw, Glide, and Inversion Molecular Aggregates and Implications for the Packing of Molecules in Monolayers and Crystals", *J. Am. Chem. Soc.*, 116, 1994, 455–470.

Reddy, A., et al., "Synthesis of x–, β–and cyclic spaglumic acids", *Int. J. Peptide Protein Res.*, 40, 1992, 472–476.

Bergeron, Raymond J., et al., "Macromolecular Self–Assembly of Diketopiperazine Tetrapeptides", *J. Am. Chem. Soc.* 116(19):8479–8484 (1994).

Borman, S., "Peptide spontaneously assembles into membrane", *Chemical & Engineering News*, May 3, 1993, 45–46.

Brumlik, C., et al., "Template Synthesis of Metal Microtubules", *Journal of the American Chemical Society*, 113, 1991, 3174–3175.

Katchalski, E., et al., "Synthesis of lysine anhydride," 68 J. Amer. Chem. Soc. 879–880 (1946).

Koppel, K. D., and H. G. Ghazarian, "A convenient synthesis of 2,5–diketopiperazinediones," 33 J. Organic Chem. 862–864 (1968).

METHOD FOR MAKING SELF-ASSEMBLING DIKETOPIPERAZINE DRUG DELIVERY SYSTEM

The present application is a continuation-in-part of U.S. Ser. No. 07/849,186, U.S. Pat. No. 5,352,461, "Self-Assembling Diketopiperazine Drug Delivery System" filed Mar. 11, 1992, by Robert Feldstein, John Glass and Solomon Steiner, the contents of which are hereby incorporated by reference.

BACKGROUND OF THE INVENTION

This invention is generally in the area of drug delivery systems and is particularly related to methods of reversible microencapsulation of drugs by certain derivatives of 2,5-diketopiperazine, modified diketopiperazine microparticles, and use thereof.

Delivery of drugs has been a major problem for many years, particularly when the compound to be delivered is unstable under the conditions encountered in the gastrointestinal tract when administered orally to a subject, prior to reaching its targeted location. For example, it is preferable in many cases to administer drugs orally, especially in terms of ease of administration, patient compliance, and decreased cost. However, many compounds are ineffective or exhibit low or variable potency when administered orally. Presumably this is because the drugs are unstable to conditions in the digestive tract or because they are inefficiently absorbed.

A variety of enteric coatings have been used to encapsulate and protect the drug prior to reaching the small intestine. In some cases these coatings are effective. However, there are drugs that are unstable to the conditions present in the small intestine and therefore must be administered in much higher dosages if the drug is to be released in the small intestine so that an effective amount is absorbed by the bloodstream. In these cases, it is necessary to have a mechanism whereby the coating is not only stable to the conditions present in the digestive tract, as well as to the conditions under which it is stored prior to administration to the patient, but which allows the encapsulated drug to pass into the bloodstream.

A broad range of delivery systems, including microparticles and microspheres, that are small enough to be administered intravenously, have been developed. It is desirable in some cases for these to be insoluble in the blood, as well as under the conditions under which the delivery system is stored prior to administration to the patient. Release of the encapsulated drug can occur following uptake by phagocytic cells. Controlled release of drug can also occur by diffusion out of the slowly degrading microparticles.

Other factors in drug delivery system design include the requirements that the system must be non-toxic, non-reactive with the drug to be delivered, not too expensive or difficult to manufacture, formed of readily available components, and consistent with respect to final composition and physical characteristics, including stability and release rate. The system must also be formed of materials that are easily removed by normal metabolic processes.

U.S. Ser. No. 07/849,186 filed Mar. 11, 1992, describes a drug delivery system based on the formation of diketopiperazine microparticles from diketopiperazine derivatives containing a single six membered ring diketopiperazine, which are stable at low pH and disintegrate at the pH present in the blood or small intestine. The drug to be delivered is encapsulated within the diketopiperazine microparticles by dissolving the diketopiperazine in a basic solution, adding the drug in solution or suspension, then solidifying the structure by adding acid.

However, it would be preferable to have other methods for forming diketopiperazine microparticles that allow for encapsulation of other materials, especially those which are not stable or soluble under the conditions disclosed in U.S. Ser. No. 07/849,186 filed Mar. 11, 1992. It would also be preferable to have microparticles made from modified diketopiperazine derivatives such that the microparticles disintegrate under a variety of conditions. It would further be preferable to be able to target the microparticles to uptake by particular cells, and conditions where release occurs only within or at the targeted cells.

It is therefore an object of the present invention to provide improved methods for making a system for drug delivery which, by intentional modifications to its structure, can be made to be stable or unstable in a variety of physiological conditions, and methods for use thereof.

It is another object of the present invention to provide methods for making a system which is self-assembling, can be manufactured economically from currently available reagents, and can be targeted to specific cells.

It is still another object of the present invention to provide a process for encapsulation of insoluble, hydrophobic, or labile drugs.

SUMMARY OF THE INVENTION

Drug delivery systems have been developed based on the formation of diketopiperazine microparticles which are stable under particular conditions and unstable under different conditions. Modifications have been developed in the process in which insoluble drugs are more readily encapsulated. Microparticles have been developed that are stable at basic pH and unstable at acidic pH, and that are stable at both acidic and basic pH, but which are unstable at pH between about 6 and 8. In another embodiment, the microparticles have been modified to allow targeting to specific cell types and to effect release only after reaching the targeted cells.

In the most preferred embodiment the microparticles are formed in the presence of the drug to be delivered, for example, proteins or peptides such as insulin and calcitonin, polysaccharides such as heparin, nucleic acid molecules, and synthetic organic pharmaceutical compounds such as felbamate or lamotrigine. The diketopiperazine microparticles are preferably formed in the presence of the drug to be encapsulated by:

(i) acidification of weakly alkaline solutions of a diketopiperazine derivative that contains one or more acidic groups, (ii) basification of acidic solutions of a diketopiperazine derivative that contains one or more basic groups, or (iii) neutralization of an acidic or basic solution of a diketopiperazine derivative that contains both acidic and basic groups.

The size of the resulting microparticles can be controlled by modifying the side-chains on the diketopiperazine, the concentration of various reactants, the conditions used for formation, and the process used in formation. The diketopiperazines can be symmetrically functionalized, wherein the two side-chains are identical, or they can be unsymmetrically functionalized. Both the symmetrically and unsymmetrically functionalized diketopiperazines can have side-chains that contain acidic groups, basic groups, or combinations thereof.

Diketopiperazines with zero, one and two protecting groups on the two side-chains each have different solubilities depending on the solvent and the solution pH, and can be isolated from solution by precipitation. Accordingly, the unsymmetrically substituted diketopiperazines can be prepared by selectively deprotecting and precipitating diketopiperazines with one side chain deprotected. The monoprotected diketopiperazine derivatives themselves tend to be soluble in acidic media and insoluble in weakly alkaline solutions.

Examples demonstrate that encapsulation and oral administration of insulin in rats results in a decrease in blood glucose. Encapsulation and oral administration of heparin results in inhibition of blood coagulation. Oral delivery of microparticles containing salmon calcitonin (sCT) reduces plasma calcium levels, and produces substantial blood levels of salmon calcitonin. Examples also demonstrate that encapsulation and intravenous administration of the anticonvulsant felbamate in mice results in control of convulsions.

DETAILED DESCRIPTION OF THE INVENTION

Figure 1:
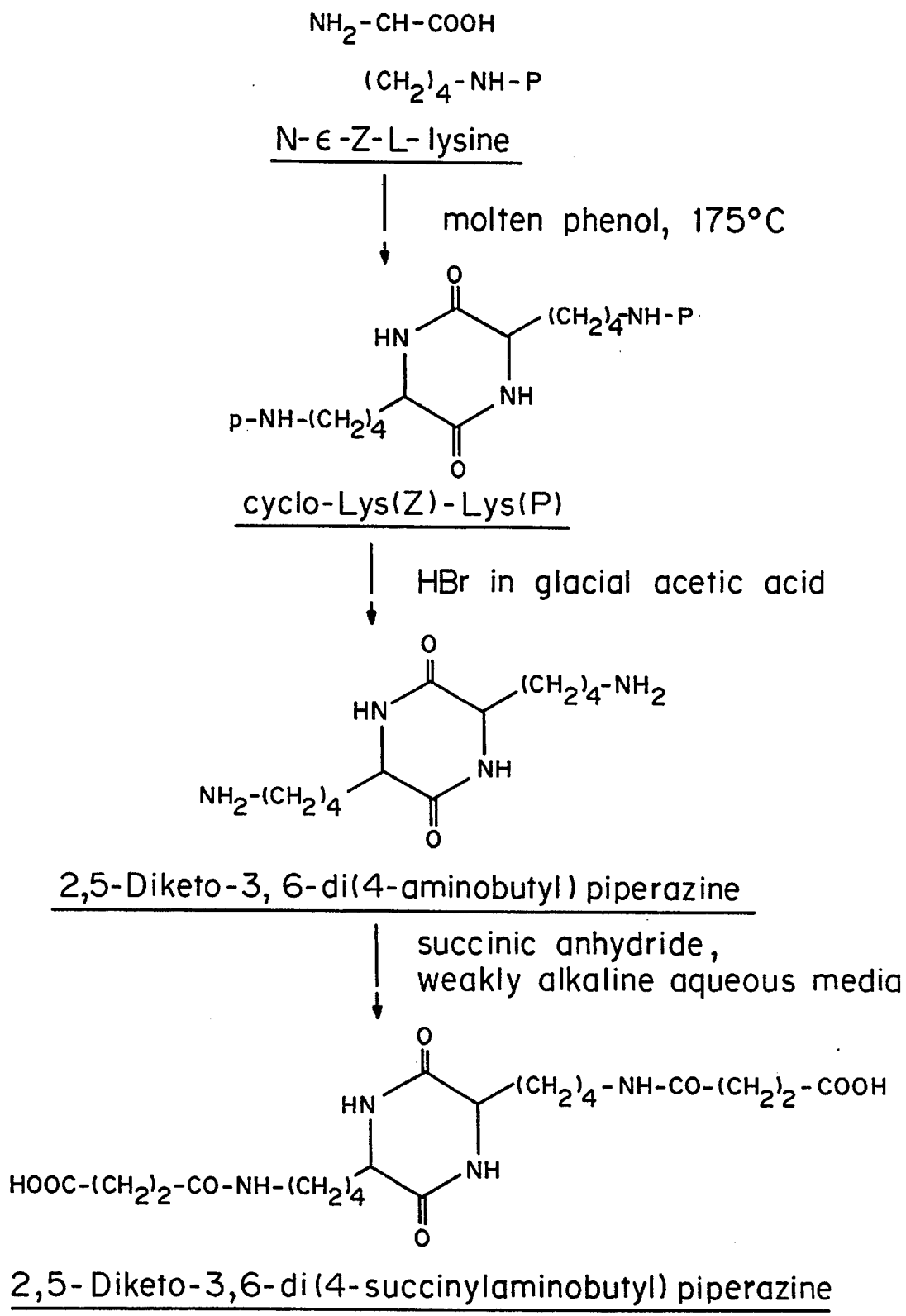
FIG. 1 is a schematic of the synthesis of 2,5-diketo-3,6-di(4-succinylaminobutyl)piperazine.

The present invention is a drug delivery system using diketopiperazines to form microparticles encapsulating a drug to be delivered.

As used herein, the term "microparticles" includes microcapsules having an outer shell surrounding a core material; microspheres containing drug dispersed throughout the sphere; and microparticles of irregular shape. In the preferred embodiment, the microparticles are microspheres of between 0.1 to ten microns in diameter.

As used herein, "drug" and "cargo" refer to the pharmacologically active agent incorporated into the microparticles.

As used herein, "acidic" refers to a pH range of between 0 and 6; "basic" refers to a pH range of between 8 and 14; "neutral" refers to a pH range of between 6 and 8; and "weakly alkaline" refers to a pH range of between 8 and 10.

A system based upon diketopiperazine or one of its substitution derivatives, including diketomorpholines and diketodioxanes, forms microparticles with desirable size distributions and pH ranges as well as good cargo tolerance. A wide range of stable, reproducible characteristics can be generated with appropriate manipulations of the attachment sites.

Diketopiperazines

The diketopiperazines or their substitution analogs containing at least six ring atoms are rings with opposing heteroatoms and unbonded electron pairs. One or both of the nitrogens can be replaced with oxygen to create the substitution analogs diketomorpholine and diketodioxane, respectively. The general formula for diketopiperazine and its analogs is shown below.

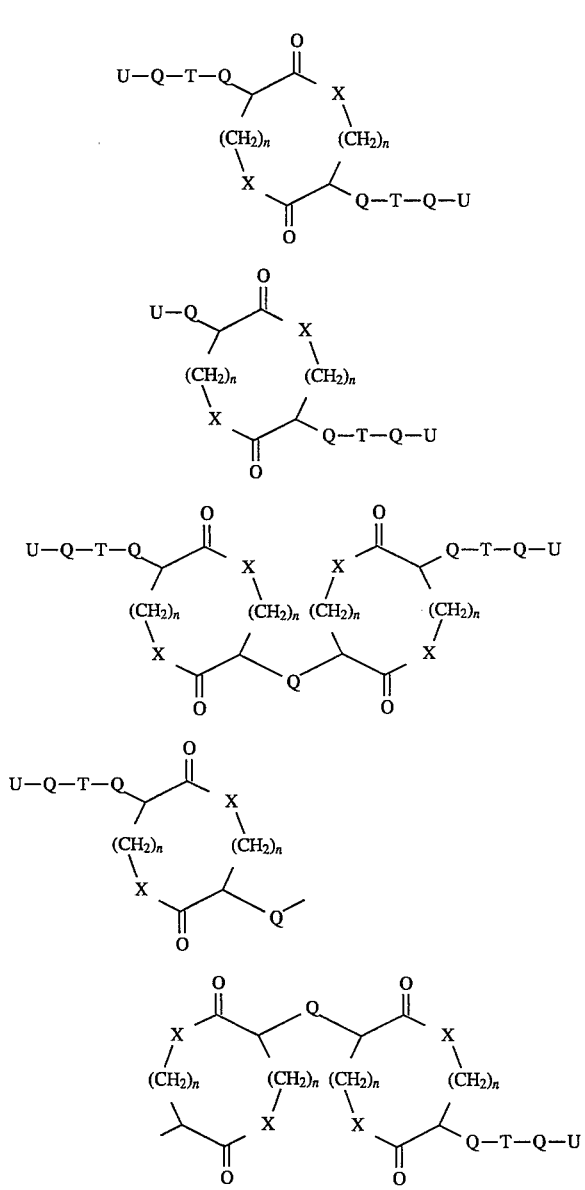

Wherein n is between 0 and 7, Q is, independently, a $C_{1-20}$ straight, branched or cyclic alkyl, aralkyl, alkaryl, alkenyl, alkynyl, heteroalkyl, heterocyclic, alkyl-heterocyclic, or heterocyclic-alkyl; T is —C(O)O, —OC(O), —C(O)NH, —NH, —NQ, —OQO, —O, —NHC(O), —OP(O), —P(O)O, —OP(O)$_2$, —P(O)$_2$O, —OS(O)$_2$, or —S(O)$_3$; U is an acid group, such as a carboxylic acid, phosphoric acid, phosphonic acid and sulfonic acid, or a basic group, such as primary, secondary and tertiary amines, quaternary ammonium salts, guanidine, aniline, heterocyclic derivatives, such as pyridine and morpholine, or a $C_{1-20}$ chain containing at least one acidic group and at least one basic group, for example, those described above, wherein the side chains can be further functionalized with an alkene or alkyne group at any position, one or more of the carbons on the side chain can be replaced with an oxygen, for example, to provide short polyethylene glycol chains, one or more of the carbons can be functionalized with an acidic or basic group, as described above, and wherein the ring atoms X at positions 1 and 4 are either O or N.

As used herein, "side chains" are defined as Q—T—Q—U or Q—U, wherein Q, T, and U are defined above.

Examples of acidic side chains include, but are not limited, to cis and trans —CH=CH—CO$_2$H, —CH(CH$_3$)=CH(CH$_3$)—CO$_2$H, —(CH$_2$)$_3$—CO$_2$H, —CH$_2$CH(CH$_3$)—CO$_2$H, —CH(CH$_2$CO$_2$H)=CH$_2$, -(tetrafluoro)benzoic acid, -benzoic acid and —CH(NH-C(O)CF$_3$)—CH$_2$—CO$_2$H.

Examples of basic side chains include, but are not limited to, -aniline, -phenyl—C(NH)NH$_2$, -phenyl—C(NH)NH(alkyl), -phenyl—C(NH)N(alkyl)$_2$ and —(CH$_2$)$_4$NHC(O)CH(NH$_2$)CH(NH$_2$)CO$_2$H.

Examples of side chains with both acidic and basic groups include, but are not limited to, —CH(NH$_2$)—CH$_2$—CO$_2$H and —NH(CH$_2$)$_{1-20}$CO$_2$H.

The term aralkyl refers to an aryl group with an alkyl substituent.

The term heterocyclic-alkyl refers to a heterocyclic group with an alkyl substituent.

The term alkaryl refers to an alkyl group that has an aryl substituent.

The term alkyl-heterocyclic refers to an alkyl group that has a heterocyclic substituent.

The term alkene, as referred to herein, and unless otherwise specified, refers to an alkene group of $C_2$ to $C_{10}$, and specifically includes vinyl and allyl.

The term alkyne, as referred to herein, and unless otherwise specified, refers to an alkyne group of $C_2$ to $C_{10}$.

As used herein, "diketopiperazines" includes diketopiperazines and derivatives and modifications thereof falling within the scope of the above-general formula.

An example of a preferred compound, 2,5-diketo- 3,6-di(4-succinylaminobutyl)piperazine, wherein X is N, n is 0 and Q is (CH$_2$)$_4$—NH—CO—(CH$_2$)$_2$—COOH, is shown below:

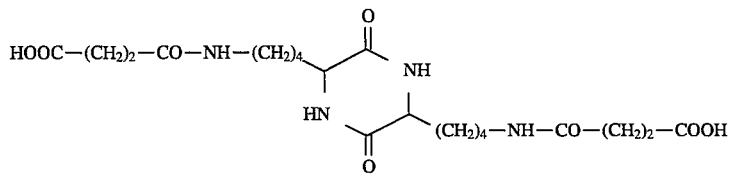

Methods for Synthesis of the Diketopiperazines

Diketopiperazines can be formed by cyclodimerization of amino acid ester derivatives, as described by Katchalski, et al., *J. Amer. Chem. Soc.* 68, 879–880 (1946), by cyclization of dipeptide ester derivatives, or by thermal dehydration of amino acid derivatives in high-boiling solvents, as described by Kopple, et al., *J. Org. Chem.* 33(2), 862–864 (1968), the teachings of which are incorporated herein. 2,5-diketo-3,6-di(aminobutyl)piperazine (Katchalski etal. refers to this as lysine anhydride) was prepared via cyclodimerization of N-epsilon-P-L-lysine in molten phenol, similar to the Kopple method in *J. Org. Chem.*, followed by removal of the protecting (P)-groups with 4.3 M HBr in acetic acid. This route is preferred because it uses a commercially available starting material, it involves reaction conditions that are reported to preserve stereochemistry of the starting materials in the product and all steps can be easily scaled up for manufacture.

Diketomorpholine and diketooxetane derivatives can be prepared by stepwise cyclization in a manner similar to that disclosed in Katchalski, et al., *J. Amer. Chem. Soc.* 68, 879–880 (1946).

Diketopiperazines can be radiolabelled. Means for attaching radiolabels are known to those skilled in the art. Radiolabelled diketopiperazines can be prepared, for example, by reacting tritium gas with those compounds listed above that contain a double or triple bond. A carbon-14 radiolabelled carbon can be incorporated into the side chain by using $^{14}C$ labelled precursors which are readily available. These radiolabelled diketopiperazines can be detected in vivo after the resulting microparticles are administered to a subject.

Synthesis of Symmetrical Diketopiperazine Derivatives

The diketopiperazine derivatives are symmetrical when both side chains are identical. The side chains can contain acidic groups, basic groups, or combinations thereof.

One example of a symmetrical diketopiperazine derivative is 2,5-diketo-3,6-di(4-succinylaminobutyl)piperazine. The synthesis of 2,5-diketo- 3,6-di(4-succinylaminobutyl)piperazine is shown schematically in FIG. 1. 2,5-diketo-3,6-di(aminobutyl)piperazine is exhaustively succinylated with succinic anhydride in mildly alkaline aqueous solution to yield a product which is readily soluble in weakly alkaline aqueous solution, but which is quite insoluble in acidic aqueous solutions. When concentrated solutions of the compound in weakly alkaline media are acidified under appropriate conditions, the material separates from the solution as microparticles.

Other preferred compounds can be obtained by replacing the succinyl group(s) in the above compound with glutaryl, maleyl or fumaryl groups.

Unsymmetrical Diketopiperazine Derivatives From Unsymmetric Deprotection of a Symmetrical Diketopiperazine Intermediate One method for preparing unsymmetrical diketopiperazine derivatives is to protect functional groups on the side chain, selectively deprotect one of the side chains, react the deprotected functional group to form a first side chain, deprotect the second functional group, and react the deprotected functional group to form a second side chain.

Diketopiperazine derivatives with protected acidic side chains, such as cyclo-Lys(P)Lys(P), wherein P is a benzyloxycarbonyl group, or other protecting group known to those skilled in the art, can be selectively deprotected. The protecting groups can be selectively cleaved by using limiting reagents, such as HBr in the case of the benzyloxycarbonyl group, or fluoride ion in the case of silicon protecting groups, and by using limiting time intervals. In this manner, reaction mixtures which contain unprotected, monoprotected and di-protected diketopiperazine derivatives can be obtained. These compounds have different solubilities in various solvents and pH ranges, and can be separated by selective precipitation and removal. An appropriate solvent, for example, ether, can then be added to such reaction mixtures to precipitate all of these materials together. This can stop the deprotection reaction before completion by removing the diketopiperazines from the reactants used to deprotect the protecting groups. By stirring the mixed precipitate with water, both the partially and completely reacted species can be dissolved as salts in the aqueous medium. The unreacted starting material can be removed by centrifugation or filtration. By adjusting the pH of the aqueous solution to a weakly alkaline condition, the asymmetric monoprotected product containing a single protecting group precipitates from the solution, leaving the completely deprotected material in solution.

In the case of diketopiperazine derivatives with basic side chains, the basic groups can also be selectively deprotected. As described above, the deprotection step can be stopped before completion, for example, by adding a suitable solvent to the reaction. By carefully adjusting the solution pH, the diprotected derivative can be removed by filtration, leaving the partially and totally deprotected derivatives in solution. By adjusting the pH of the solution to a slightly acidic condition, the monoprotected derivative precipitates out of solution and can be isolated.

Diketopiperazine derivatives containing combinations of acidic and basic side chains can also be selectively deprotected, as described above. In the last step, adjusting the pH to a slightly acidic condition precipitates the monoprotected compound with a free acidic group. Adjusting the pH to a slightly basic condition precipitates the monoprotected compound with a free basic group.

The monoprotected diketopiperazine is reacted to produce a diketopiperazine with one side chain and protecting group. Removal of the protecting group and coupling the resulting deprotected functional group with other side chains yields unsymmetrically substituted diketopiperazines with various combinations of acidic or basic side chains, and side chains containing a combination of acidic and basic groups.

Other materials that exhibit this response to pH can be obtained by functionalizing the amide ring nitrogens of the diketopiperazine ring. The ring nitrogens can be functionalized, for example, by reaction with carboxylic acid derivatives, sulfonic acid derivatives and alkylating agents.

Modifying the Diketopiperazines with Targeting Molecules

The functional groups on the diketopiperazine side chains can be modified by covalently coupling a poly(alkylene glycol) such as poly(ethylene glycol), proteins, peptides, oligosaccharides, carbohydrate, lipids, nucleotide sequences or other molecules to target microparticles made from the diketopiperazines to specific regions of the body or to certain cell types.

The targeting molecule can be, for example, a protein or peptide such as a hormone, antibody or antibody fragment, such as the Fab or $Fab_2$ antibody fragments, or a specific cell surface receptor ligand, lipid, polysaccharide, nucleic acid, carbohydrate, a combination thereof, or other molecule, including a synthetic molecule, that identifies and localizes at the target material.

Targeting molecules can be chemically coupled to the diketopiperazines forming the microparticles, or incorporated onto or into the microparticles at the time of formation.

The coupling involves forming ester, thioester, amide, or sulfamide linkages. Methods for coupling hydroxy, thio, or amine groups with carboxy or sulfoxy groups are known to those skilled in the art.

The diketopiperazines can contain various functional groups, such as hydroxy, thio, and amine groups, that can react with a carboxylic acid or carboxylic acid derivative under the coupling conditions. Reactive functional groups not involved in the coupling chemistry must be protected to avoid unwanted side reactions. After the carboxylic acid or derivative reacts with a hydroxy, thio, or amine group to form an ester, thioester, or amide group, any protected functional groups can be deprotected by means known to those skilled in the art.

The term "protecting group" as used herein refers to a moiety which blocks a functional group from reaction, and which is cleavable when there is no longer a need to protect the functional group. Suitable protecting groups for the hydroxyl group include certain ethers, esters and carbonates (Greene, T. W. and Wuts, P. G. M., "Protective groups in organic synthesis," John Wiley, New York, 2nd Ed. (1991)). Suitable protecting groups for the carboxyl group include those described in Green and Wuts, Protecting Groups in Organic Synthesis, John Wiley (1991). Side-chain functionalities such as carboxylic acids, alcohols, and amines may interfere with the coupling chemistry and must be appropriately protected.

As used herein, "side-chain functionality" refers to functional groups, such as hydroxy, thio, amine, keto, carboxy, alkenyl, alkynyl, carbonyl, and phosphorus derivatives such as phosphate, phosphonate and phosphinate in the diketopiperazines or material to be covalently attached to the diketopiperazines, that is not involved in coupling to form an ester, thioester, amide or sulfamide bond. Examples of suitable protecting groups are well known to those skilled in the art. See, generally, Greene and Wuts, Protecting Groups in Organic Chemistry, John Wiley (1991).

Examples of protecting groups for amine groups include t-butyloxycarbonyl (Boc), benzyloxycarbonyl (Cbz).

Amine groups on diketopiperazines can be coupled with amine groups on a peptide by forming a Schiff base, using coupling agents such as glutaraldehyde. An example of this coupling is described by Allcock, et al., *Macromolecules*, Vol. 19(6), pp. 196 (1986), hereby incorporated by reference. Amine groups can also be coupled with DCC or other dehydrating agents, as described above, with carboxy groups on amino acids, proteins or peptides.

Alternatively, one can incorporate amino acids, proteins, or peptides into the diketopiperazines by displacing chlorines on chlorine-containing side-chains on the diketopiperazines.

Additionally, amine groups can be converted to diazonium salts, which can be reacted with amine or hydroxy groups on biological materials. An example of this coupling is described by Allcock, et al., *Macromolecules*, Vol. 16(9), pp. 1405 (1983), hereby incorporated by reference.

Methods for Forming Microparticles and Encapsulating Drug

In one embodiment, drug is encapsulated within microparticles by dissolving a diketopiperazine with acidic side chains in bicarbonate or other basic solution, adding the drug to be encapsulated in solution or suspension, then precipitating the diketopiperazine to form microparticles by adding acid, such as citric acid.

In a second embodiment, drug is encapsulated within microparticles by dissolving a diketopiperazine with basic side chains in an acidic solution, such as citric acid, adding the drug to be encapsulated in solution or suspension, then precipitating the diketopiperazine to form microparticles by adding bicarbonate or other basic solution.

In a third embodiment, drug is encapsulated within microparticles by dissolving a diketopiperazine with both acidic and basic side chains in an acidic or basic solution, adding the drug to be encapsulated in solution or suspension, then precipitating the diketopiperazine to form microparticles by neutralizing the solution.

The microparticles can be stored in the dried state and suspended for administration to a patient. In the first embodiment, the reconstituted microparticles maintain their stability in an acidic medium and dissociate as the medium approaches physiological pH in the range of between 6 and 14. In the second embodiment, suspended microparticles maintain their stability in a basic medium and dissociate as the medium approaches pH in the range of between 0 and 6. In the third embodiment, the reconstituted microparticles maintain their stability in an acidic or basic medium and dissociate as the medium approaches physiological pH in the range of between 6 and 8.

Materials That Can Be Encapsulated

For drug delivery, biologically active agents having therapeutic, prophylactic or diagnostic activities can be delivered. These can be organic or inorganic compounds, proteins, or a wide variety of other compounds, including nutritional agents such as vitamins, minerals, amino acids and fats. In the preferred embodiments, the materials are biologically active agents that are to be released in the circulatory system after transport from the GI tract following oral delivery. Examples include proteins and peptides (wherein protein is defined as consisting of 100 amino acid residues or more and a peptide is less than 100 amino acid residues), such as insulin and other hormones, polysaccharides, such as heparin, nucleic acids, such as antisense oligonucleotides, lipids and lipopolysaccharides, and organic molecules. Preferably, these materials have a molecular weight between 100 and 500,000 g/mol. Specific examples of materials to be delivered include hormones, anticoagulants, immunomodulating agents, cytotoxic agents, antibiotics, vasoactive agents, neuroactive agents, anaesthetics or sedatives, steroids, decongestants, antivirals, antisense, antigens, and antibodies. More particularly, these compounds include insulin, heparin, calcitonin, felbamate, parathyroid hormone and fragments thereof, growth hormone, erythropoietin, AZT, DDI, G CSF, lamotrigine, chorionic gonadotropin releasing factor, luteinizing releasing hormone, $\beta$-galactosidase and Argatroban.

Biological agents which are unstable in gastric acid, diffuse slowly through gastrointestinal membranes, and/or are susceptible to enzymatic destruction in the gastrointestinal tract can be delivered in the microparticles described herein with high efficiency and retention of biological activity. The system is also especially useful where the biological agents are either unstable in the blood, or need to be targeted to phagocytic cells.

Hydrophobic molecules or molecules that are insoluble in aqueous media at clinically relevant concentrations, such as felbamate, can be encapsulated in microparticles. Thus, the hydrophobic or insoluble molecules encapsulated in the microparticles can be administered intravenously and dispersed into media such as blood. Since the microparticles release the hydrophobic or insoluble drugs at a controlled rate, the drugs do not precipitate from the blood (for example, at the site of injection or elsewhere) and form a clot in the vessels.

In the preferred embodiments, the protective material, the diketopiperazines, are not biologically active and do not alter the pharmacologic properties of the therapeutic agents.

For acidic drugs, salts of metals, amines or organic cations of acidic drugs can in some cases be used. Simple derivatives of the drugs, such as ethers, esters, and amides, which have desirable retention and release characteristics, can also be used.

Imaging agents including metals, radioactive isotopes, radioopaque agents, fluorescent dyes, and radiolucent agents can also be incorporated. Radioisotopes and radioopaque agents include gallium, technetium, indium, strontium, iodine, barium, and phosphorus containing compounds.

Pharmaceutical Compositions

The microparticles can be administered in suspension or encapsulated in another material such as an enteric coating or stabilizing agent such as albumin or lactose. These materials and methods for use thereof are well known to those in the pharmaceutical industry. The pharmaceutical composition may consist only of the microparticles or may further include the encapsulated compound, or other compounds. For example, it may be desirable to administer a compound that is stable to passage through the stomach that is then rapidly absorbed in one dosage in the intestine, followed by the more controlled, delayed release of the same or a different compound from the microparticles, such as enterically protected basic stable, neutral, soluble microcapsules.

The microparticles can be administered topically, locally or systemically by parenteral administration or enteral administration.

The microparticles of the first embodiment are stable to acid and resist the acidic environment of the stomach. In addition, they are resistant to enzymatic degradation in the stomach. They are believed to pass through the endothelium into the blood stream where they become soluble in the near neutral pH of the blood, liberating the pharmacologically active compound.

The microparticles of the second embodiment are stable to basic and neutral environments, and hence are stable within the environment of the blood. They then dissociate when subjected to acidic pH, for example, in the interior of phagocytic cells.

The microparticles of the third embodiment are stable to neutral environments, and hence are stable in the blood (pH approximately 7.2 to 7.4) and small intestine (pH approximately 6.8 to 7.2).

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Enteral Administration

Microparticles having biologically active agents are preferably administered orally, for example, as tablets, pills, capsules, or troches. These microparticles, depending on the chemical nature and size, will either be absorbed to, or passed through, the epithelial lining of the gastrointestinal tract into the bloodstream or lymphatic system. These can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier. In addition, dosage unit forms can contain various other materials which modify the physical form of the dosage unit, for example, coatings of sugar, shellac, or other enteric agents.

Parenteral Administration

Microparticles of less than five microns readily pass through a needle for intravenous administration. Suitable pharmaceutical carriers, for example, saline solution, are known and commercially available. Intravenous administration may be preferred for targeted delivery of incorporated compounds to phagocytic cells, for example, of antiparasitic or anti-HIV drugs, where the drug is also selective for these cell types. Microparticles should be stable at neutral pH, for example, for site specific drug delivery to phagocytic cells, or to slowly dissolve at neutral pH so release occurs uniformly throughout the bloodstream.

Hydrophobic molecules or molecules that are insoluble in aqueous media at clinically relevant concentrations can be encapsulated in microparticles, administered intravenously and dispersed into media such as blood. When administered in microparticles, the drugs do not precipitate from the blood (for example, at the site of injection or elsewhere) and form a clot in the vessels.

Subcutaneous, Intramuscular and Intraperitoneal Administration

Microparticles produced as described above are small enough to be injected through a standard gauge needle under the skin or into the peritoneum for subsequent release of incorporated drug, generally less than 100 microns in diameter, more typically less than 20 microns, and most preferably, less than 5 microns. Adhesion of the microparticles to the peritoneum aids in localizing release of the incorporated drug. Microparticles can also be implanted or injected intramuscularly for immunization or other purposes where slower release into the bloodstream is desirable. Carriers such as phosphate buffered saline, or an adjuvant such as an oil, can be used as a carrier for the microparticles. Pharmaceutically acceptable carriers are known to those skilled in the art.

Topical Administration

Microparticles are suspended in a suitable pharmaceutical carrier for administration using methods appropriate for the carrier and site of administration. For example, microparticles are administered to the eye in a buffered saline solution, approximately pH 7.4, or in an ointment such as mineral oil. The dosage will be dependent on the compound to be released as well as the rate of release. The microparticles, or aggregations of microparticles into films, disks, or tablets, with incorporated compound can be administered to the skin in an ointment or cream. Suitable pharmaceutical carriers are known to those skilled in the art and are commercially available.

Sustained delivery of antibiotics or growth factors (amino acids, peptides, or protein growth factors) to open wounds is of particular therapeutic importance in a variety of medical and surgical situations including thermal burns, chemical burns, surgical wounds, diabetic ulcers and vascular insufficiency.

Diagnostic Applications

The microparticles containing radioopaque compounds, such as barium, radioisotopes, radiolucent compounds, magnetic materials or fluorescent materials are particularly suited for use in diagnostic procedures. The microparticles can be administered parenterally or enterally. Microparticles that bind to mucosal membranes are particularly preferred for these applications, especially for imaging of the nasal and pharyngeal, gastrointestinal, and genitourinary tracts. Intravenous administration of microparticles containing imaging agents are particularly useful for imaging liver, spleen or lung.

Targeted Administration

The microparticles can be delivered to specific cells, especially phagocytic cells and organs. Phagocytic cells within the Peyer's patches appear to selectively take up microparticles administered orally. Phagocytic cells of the reticuloendothelial system also take up microparticles when administered intravenously. Microparticles of less than five microns diameter can be injected without embolytic complications. Endocytosis of the microparticles by macrophages can be used to target the microparticles to the spleen, bone marrow, liver and lymph nodes.

The charge or lipophilicity of the microparticle is used to change the properties of the protein carrier. For example, the lipophilicity can be modified by linking lipophilic groups to increase solubility of some drugs, thereby increasing drug cargo capacity. Other modifications can be made before or after formation of the microparticle, as long as the modification after formation does not have a detrimental effect on the incorporated compound.

The present invention will be further understood by reference to the following non-limiting examples of the preparation and administration of diketopiperazine microparticles containing insulin, heparin, salmon calcitonin and felbamate.

Example 1

Preparation of the succinyl diketopiperazine derivative and resulting microparticles.

Formation of cyclo-Lys(Z)-Lys(Z)

The method of synthesis is shown schematically in FIG. 1.

The methods of Ephraim Katchalski, Issac Grossfeld, and Max Frankel, "Synthesis of lysine anhydride" *J. Am. Chem. Soc.* 68, 879–880 (1946) and Kenneth D. Kopple and Hayop G. Ghazarian, "A convenient synthesis of 2,5-diketopiperazines" *J. Org. Chem.* 33, 862–864 (1968) were adapted for use as follows. Katchalski, et al describe the synthesis of the target compound by a different synthetic route; Kopple, et al describe a synthetic method similar to that used herein, but not using a lysine-based dipeptide nor yielding the same target compound. The letter "P" is used to designate a protecting group such as a benzyloxycarbonyl or carbobenzoxy group used to protect the amino group. Protecting groups for amines are well known to those skilled in the art.

N-epsilon-Z-L-lysine (Z=CBz) (Sigma Chemical Co, St. Louis, Mo., 50 grams) was cyclized as follows. 250 grams of crystalline phenol in a 500 mL resin reaction kettle under a gentle flow of nitrogen gas (prepurified grade) was heated to 175° C. (heating mantle). The N-epsilon-Z-L-lysine was added to the stirring phenol and held at that temperature under nitrogen for 18 hours. The reaction kettle was removed from the heating mantle and allowed to cool until the outside of the vessel was not warm to the touch and crystals were just beginning to form in the reaction mixture. The reaction mixture was then mixed with 1.5 L anhydrous ether with stirring to precipitate a fine, white powder. This precipitate was collected on a sintered glass funnel (coarse) and washed on the filter with anhydrous ether. After air drying on the filter, the product weighed 33.7 grams. A portion of the product (5 grams) was separated for analysis and purified, as follows. The material was dissolved in 50 mL of hot glacial acetic acid and the solution was filtered to remove a small amount of insoluble material. On cooling, a solid crystallized from the acetic acid solution. This material was collected by filtration, then suspended in 200 mL 1:1 water:methanol. The suspension was brought to gentle reflux, then allowed to stand at room temperature for 2 days. The purified product was collected by filtration and air dried on the filter. This procedure yielded 3.7 grams of purified cyclo-Lys(Z)-lys(z).

2,5-diketo-3,6-di(4-aminobutyl)piperazine Dihydrobromide

To deprotect and produce terminal amino groups on the side chains, twenty grams of cyclo-Lys(Z)-Lys(Z) (finely powdered) was suspended in 50 mL of glacial acetic acid, with stirring. To this suspension was added 50 mL of 4.3M HBr in glacial acetic acid to remove the carbobenzoxy-groups. For a time there was a rapid evolution of gas (carbon dioxide) and the solid dissolved almost completely; then a solid product began to separate from the reaction mixture.

Two hours after addition of the HBr solution, 150 mL of anhydrous ether was added to the mixture to complete precipitation of the product. The precipitated product was washed repeatedly with ether, then dried under a stream of dry nitrogen. The deprotected intermediate was used directly for succinylation.

2,5-diketo-3,6-di(4-succinylaminobutyl)piperazine

The dihydrobromide salt from the preceding procedure was acylated with succinic anhydride to produce 2,5-diketo-3,6-di(4-succinylaminobutyl)piperazine. First, the dihydrobromide salt was dissolved in 200 mL of solution made by saturating water with sodium bicarbonate at room temperature. This dissolution was done slowly so that carbon dioxide gas could escape without causing the mixture to foam out of the reaction vessel. The solution was filtered to remove a small amount of insoluble material and the filter was washed with an additional 50 mL of saturated sodium bicarbonate solution which was added to the filtrate.

The solution was stirred with an efficient magnetic stirrer and with continuous monitoring of the pH using a glass electrode. The initial pH was 8.7. Succinic anhydride (30 grams) was added in ten portions. Each time the pH of the reaction mixture fell to 7.5, it was readjusted to 8.7 with 4M NaOH. The pattern of adding succinic anhydride and readjusting the pH was continued until all of the succinic anhydride was dissolved and the final pH stabilized (about thirty minutes after addition of the last portion of succinic anhydride).

To precipitate the microparticles, citric acid (10 grams) was added to the reaction mixture, then the pH was slowly adjusted to 2.2 with concentrated HCl. (There is a vigorous evolution of carbon dioxide during this process, which is controlled by slow addition of the HCl). At about pH 3–3.5, a solid product began to separate from the solution. At pH 2.2 the solution was filled with fine particles. The mixture was placed in the refrigerator overnight, then the product was collected by filtration, washed with water, and air dried on the filter. The yield was 11.7 grams of off-white powder.

A small sample of the product was dissolved in the minimum volume of water at the boiling point. The solid that separated on cooling was collected by centrifugation, washed with water, then lyophilized from a centrifugal pellet.

Example 2

Preparation of Fumaryl Derivatives of Diketopiperazine

The carbobenzoxy carbonyl (CBz) protected lysine (N-Z-lysine) was dimerized in m-cresol at 140–160° C. The material was precipitated and washed with methanol. The E-amino protecting groups were removed using $H_2$ gas over a palladium on carbon (10%) catalyst to provide the diamine salt. The nitrophenyl ester or acid chloride of monoethyl fumarate was coupled to the diamine to form a diketopiperazine core ring with two ester side chains. The ethyl groups of the ester were removed by treatment with sodium hydroxide to form a dicarboxylic acid. Proton NMR spectroscopy was consistent with the structure assigned.

Example 3

Suppression of Blood Glucose Levels by oral administration of insulin

Method

Porcine insulin (Sigma Chemical Co., St. Louis, Mo., Catalog No. 1 3505, specific activity: approximately 24 IU/mg) was encapsulated in 2,5-diketo- 3,6-di (4-fumarylamino)piperazine, prepared using the same method in Example 1, by dissolving the diketopiperazine in sodium bicarbonate to form a solution containing 12.5 mg diketopiperazine/ml solution. This solution was then mixed with an equal volume of citric acid solution containing porcine insulin at a concentration of 0.172 mg insulin/ml citric acid to form a white precipitate. The product was collected by centrifuge and washed once with 200 ml of deionized water, and then dried overnight in the lyophilizer. The product was assayed by HPLC and found to contain 1.6% insulin by weight.

In total, three male rats weighing about 200 g each were each administered a dose of 100 μg insulin/kg body weight. The dose was given subcutaneously and also as insulin encapsulated in diketopiperazine. Control animals received only the diketopiperazine and the vehicle, phosphate buffered saline. Blood glucose levels were measured on samples taken from the tail vein at various times after treatment and measured as mg of glucose/dl blood using one drop of tail blood squeezed onto a Glucofilm™ strip.

Results

Figure 2A:
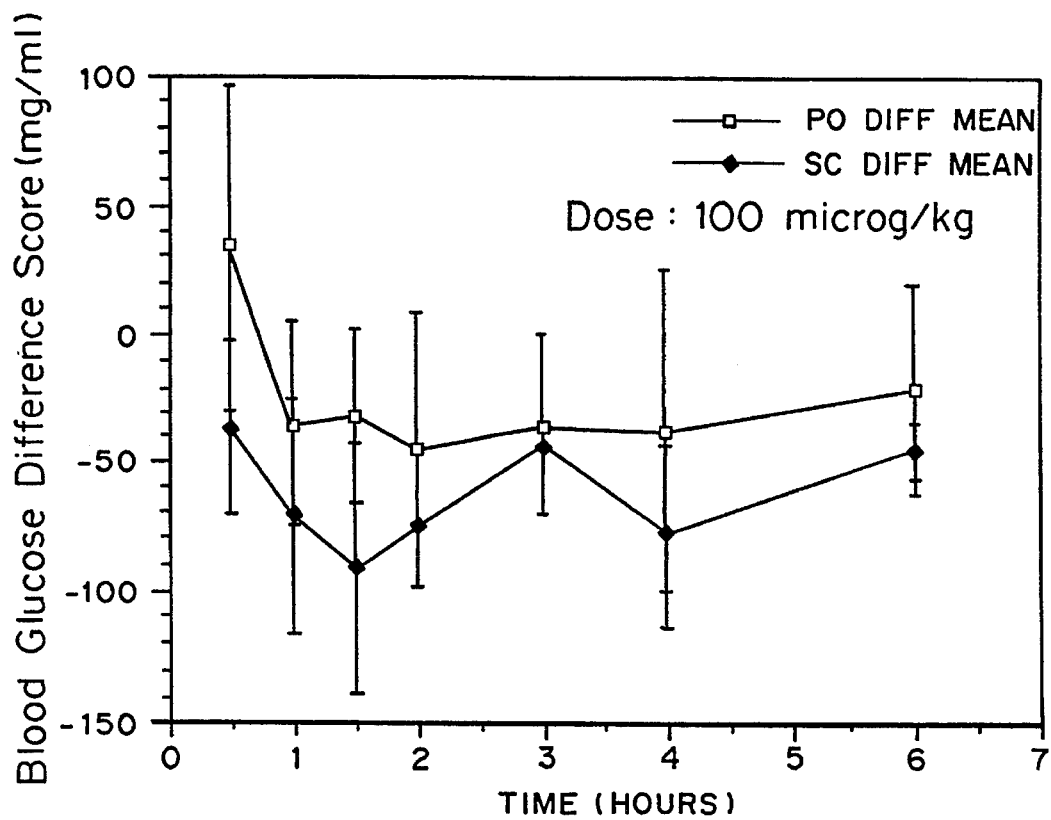
FIG. 2a is a graph of the average percent reduction in blood glucose levels measured in mg/ml for rodents receiving naked insulin and insulin/microparticles (1.6% by weight) at a dose of 100 µg insulin/kg of body weight at various time intervals (hours). The squares represent the mean difference following oral administration, and the circles represent the mean difference following subcutaneous administration.
Figure 2B:
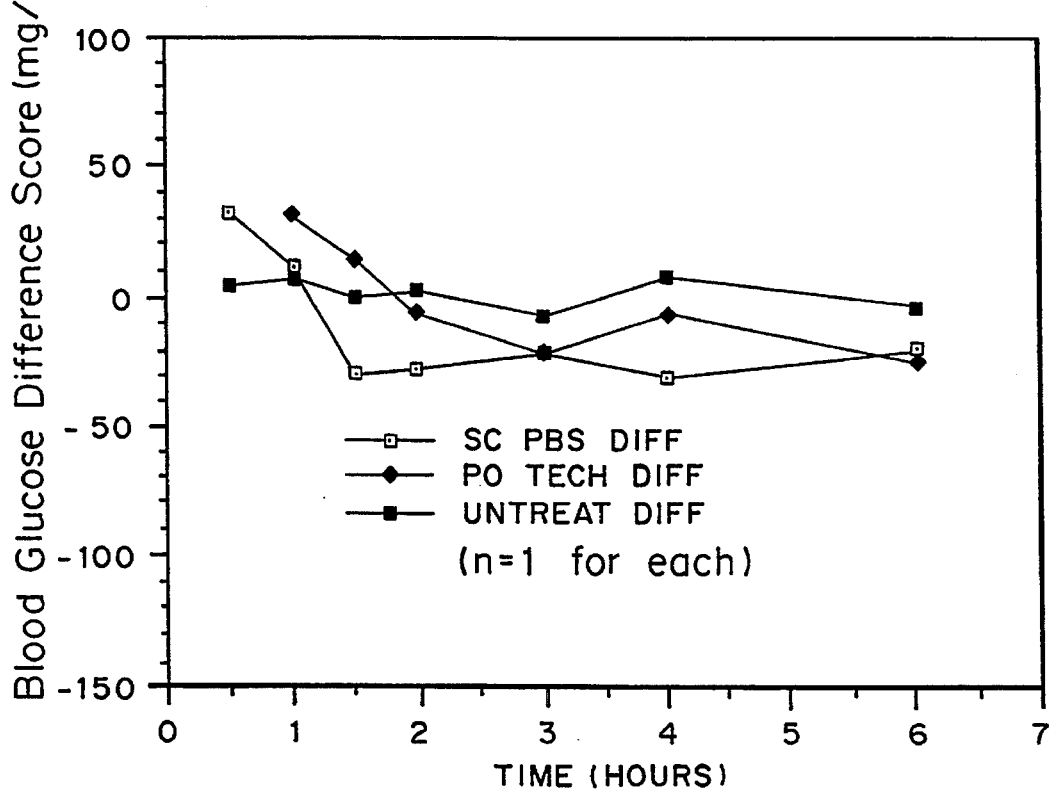
FIG. 2b is a graph of the average percent reduction in blood glucose in rodents measured in mg/ml over time (hours), following administration of the microparticles not containing insulin (controls). The squares represent the difference following subcutaneous administration of phosphate buffered saline vehicle, the circles represent the difference following oral administration of microspheres alone and the darkened squares represent the difference in untreated animals.

FIG. 2a shows the blood glucose level difference scores of animals administered encapsulated insulin by subcutaneous injection or insulin encapsulated in the diketopiperazine administered orally. A marked decrease in blood glucose level can be seen. FIG. 2b shows blood glucose level difference scores of animals administered the diketopiperazine and vehicle. No decrease in glucose level in these two animals could be detected.

Example 4

Inhibition of Clotting in Blood by Microencapsulated Heparin

Heparin (Sigma Chemical Co., St. Louis, Mo., specific activity approximately 26 U/mg)) was encapsulated as described above by dissolving 2,5-diketo- 3,6-di(4-succinylaminobutyl)piperazine, prepared as described in Example 1, in a saturated sodium bicarbonate solution to a concentration of 120 mg diketopiperazine/mL of solution, then mixing this with an equal volume of 1M citric acid containing 100 mg sodium heparin/mL citric acid.

The final suspension contained 50 mg of heparin/ml of suspension. Approximately 20% was encapsulated, yielding a theoretical maximum concentration of encapsulated heparin of 10 mg of heparin per ml of suspension.

The solution containing encapsulated heparin was administrated to eight rats weighing approximately 250 grams, by oral gavage. The rats were fasted overnight prior to treatment. Each rat received 1 ml of suspension per kg of body weight. Additionally, a suspension of microparticles formed in 1M citric acid with no heparin present was administered to a group of four (4) control rats.

Figure 3A:
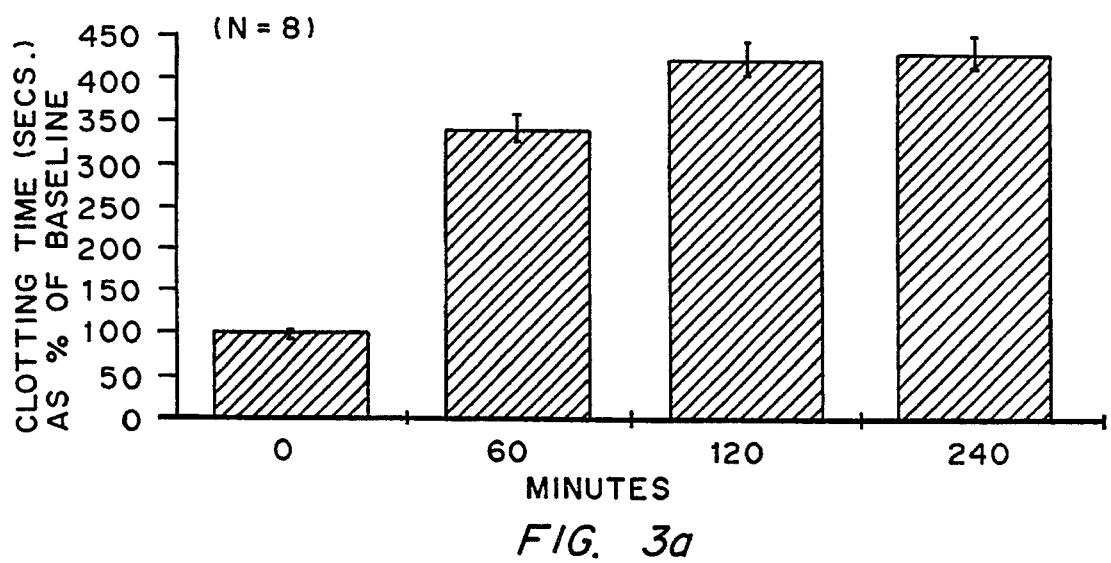
FIG. 3a is a graph of the plasma clotting time (seconds) as % of baseline over time (minutes) for plasma in rodents which have received encapsulated heparin by oral gavage.

At zero minutes, sixty minutes, one hundred and twenty minutes, two hundred and forty minutes, and three hundred and sixty minutes, blood was drawn into a citrated syringe in a ratio of 9:1 blood:citrate. The blood was immediately centrifuged and the plasma assayed using the activated partial thromboplastin time (APTT) assay with standard reagents. The results are shown in FIG. 3a. The results demonstrate that the oral administration of heparin was effective in prolonging clotting times.

Figure 3B:
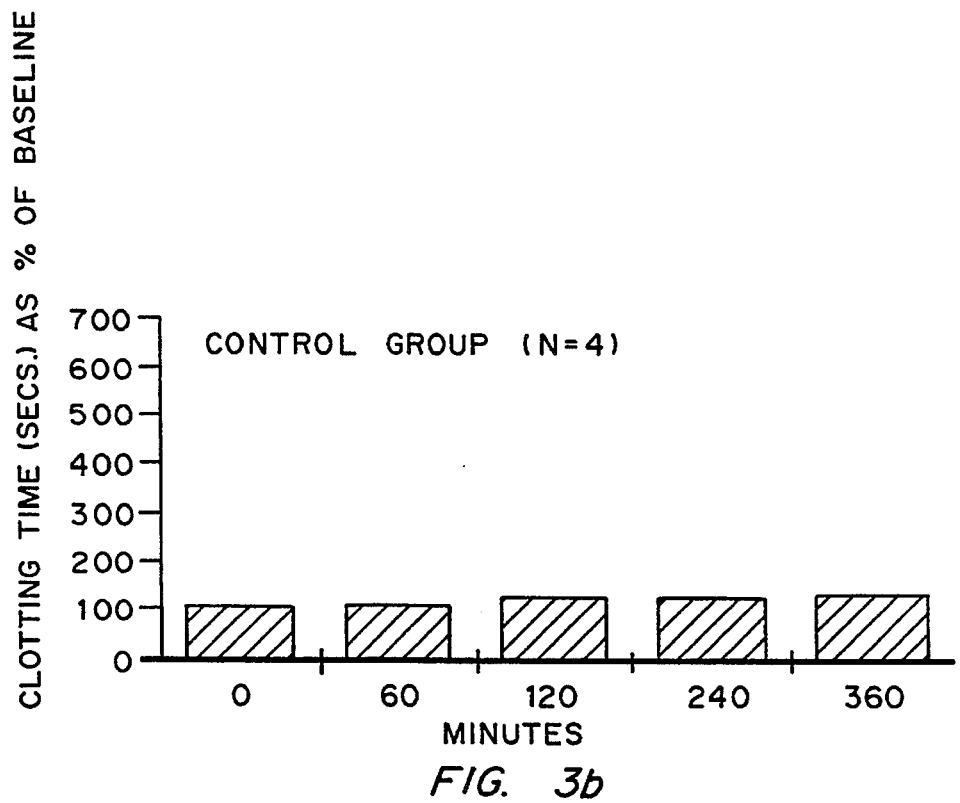
FIG. 3b is a graph of the plasma clotting time (seconds) as % of baseline over time (minutes) in rodents which have received microparticles not containing heparin by oral gavage.

FIG. 3b shows the results of the control group. The results demonstrate that the microparticles themselves do not appreciably affect clotting time.

Example 5

Encapsulation of Felbamate in Diketopiperazine Microparticles

Felbamate was encapsulated in 2,5-diketo-3,6-di(4-fumarylaminobutyl)piperazine by adding 1.6 grams of jet-milled, micronized felbamate (Carter-Wallace, Lot 3139-134) to 320 mL of a 0.5% solution of sodium lauryl sulfate in 0.1M sodium bicarbonate. To this suspension was added 4 grams of 2,5-diketo-3,6-di(4-fumarylaminobutyl)piperazine. The final suspension was placed under a probe sonicator and sonicated over a one minute period while 320 mL of 0.1M citric acid was added. The suspension was sonicated for an additional five minutes at room temperature, at which time precipitation of the microparticles was complete. The particles were isolated by centrifugation at 10,000 rpm for ten minutes, and the sample was lyophilized at room temperature overnight. The yield after drying was 4.56 grams, containing 23.7 weight percent felbamate. The total recovery of the 2,5-diketo-3,6-di(4-fumarylaminobutyl)piperazine was 87%. The felbamate content was measured by HPLCo

Example 6

Analysis of the Size of Fumaryl Microparticles

The diketopiperazine microparticles have a size of about 2 microns, as determined by scanning electron microscopy (SEM), visible light microscopy with image analysis, laser light scattering, laser diffraction and Coulter counter techniques.

Image analysis of light microscopic images shows that the particles are quite spherical (roundness 1.36, wherein the roundness of the particle is defined as the ratio of the major to minor axis diameter resulting in a roundness factor of 1.0 for a perfect sphere).

Example 7

Administration of Felbamate-Containing Microparticles to Mice and Suppression of Convulsions

Methods

Male mice (CF1, between 25 and 35 grams) obtained from Charles River were used in all experiments. Mice received microparticle encapsulated felbamate (intravenous, 100 mg/kg felbamate) in the requisite volume (0.50 mL) of 0.9% saline (pH 6.2) or 10% polyethylene glycol and 0.9% saline (pH 6.2). The microparticles were prepared from 2,5-diketo-3,6-di(4-fumarylaminobutyl)piperazine. Control animals were either untreated or received an equal volume of vehicle [0.9 % saline (pH 6.2) or 10% polyethylene glycol and 0.9 % saline (pH 6.2)] or empty microparticles in vehicle. Intravenous administration was performed by infusion into the tail vein over a 3.5 minute period using a 1 mL syringe and a 25 gauge ¾ needle attached to 12" tubing with multiple sample Luer adapter (Becton Dickinson Vacutainer System, Rutherford, N.J.). At the appropriate time (between thirty and one hundred and twenty minutes) following intravenous drug or vehicle, animals were challenged with subcutaneous pentylenetetrazol (PTZ, 85 mg/kg, between 0.25 and 0.5 mL) and observed for thirty minutes for the presence or absence of a minimal seizure (between three and five seconds of sustained clonus was indicative of a minimal threshold seizure, Swinyard, et al., 1982).

Results

Table 1, Effect of Microparticle/Felbamate Intravenous Administration on Anticonvulsant Activity in Mice, shows that the microparticle-encapsulated felbamate effectively inhibited seizures when injected intravenously.

TABLE 1

The Effect of Microparticle/Felbamate on Maximal Electroshock Seizures (MES) in Mice Following I.V. Administration Time: 15 min.

| Dose: (mg/kg): | 20 | 37.5 | 50 | | $ED_{50}$: 34.2 |
| --- | --- | --- | --- | --- | --- |
| #Prot/#Test | 1/8 | 3/8 | 8/8 | | 95% C.I.: 24.2–43.7 |
| | | | | | Slope: 6.47 ± 2.18 |
| Time: 30 min. | | | | | |
| *Dose (mg/kg): | 20 | 25 | 37.5 | 50 | $ED_{50}$: 27.2 |
| #Prot/#Test | 2/8 | 3/8 | 6/8 | 8/8 | 95% C.I.: 20.8–33.4 |
| | | | | | Slope: 6.39 ± 1.96 |
| Dose: (mg/kg) | 0 | | | | |
| #Prot/#Test | 0/8 | | | | |
| Time: 1 hr | | | | | |
| Dose: (mg/kg): | 25 | 37.5 | 50 | | $ED_{50}$: 34.9 |
| #Prot/#Test | 1/8 | 5/8 | 7/8 | | 95% C.I.: 26.6–43.1 |
| | | | | | Slope: 7.71 ± 2.66 |
| Time: 2 hr | | | | | |
| Dose: (mg/kg): | 37.5 | 50 | 60 | | $ED_{50}$: 47.3 |
| #Prot/#Test | 1/8 | 5/8 | 7/8 | | 95% C.I.: 39.2–54.5 |
| | | | | | Slope: 11.3 ± 3.89 |

*Microparticles alone: 193.4 mg/kg (equivalent microparticle material in the 60 mg/kg dose of microparticle/felbamate, which was the highest dose tested in the MES model). C.I. = confidence interval. #Prot/#Test = number of mice protected/number of mice tested. The slope is from the plot of the dose versus number of mice protected/number of mice tested.

Microparticles made from fumaryl diketopiperazine derivatives and incorporating felbamate were also shown to have an effect on maximal electroshock seizures (MES) in mice following I.V. application. Electric shocks were administered to mice fifteen minutes, thirty minutes, one hour, and two hours after microparticles containing felbamate were administered to the mice. The effect of microparticle/felbamate on maximal electroshock seizures in mice following intravenous administration is summarized above in Table 1.

As shown in Table 1, after fifteen minutes, at a dose of 20 mg/kg, one of eight mice was protected from seizures; at 37.5 mg/kg, three of eight mice were protected; at 50 mg/kg, eight of eight mice were protected. The $ED_{50}$ was determined to be 34.2 (95% Confidence Interval [CI]=24.2–43.7, slope=6.47±2.18).

After thirty minutes, at a dose of 20 mg/kg, two of eight mice were protected; at 25 mg/kg, three of eight mice were protected; at 37.5 mg/kg, six of eight mice were protected; and at 50 mg/kg, eight of eight mice were protected. The $ED_{50}$ was determined to be 27.2 mg/kg (95% CI=20.8–33.4, slope=6.39±1.96).

After one hour, at a dose of 25 mg/kg, one of eight mice was protected; at a dose of 37.5 mg/kg, five of eight mice were protected; and at 50 mg/kg, seven of eight mice were protected. The $ED_{50}$ was determined to be 34.9 mg/kg (95% CI=26.6–43.1, slope=7.71±2.66).

After two hours, at a dose of 37.5 mg/kg, one of eight mice was protected; at a dose of 50 mg/kg, five of eight mice were protected, and at 60 mg/kg, 7 of eight mice were protected. The $ED_{50}$ was determined to be 47.3 mg/kg (95% CI=39.2–54.5, slope=11.3±3.89).

These results demonstrate that the peak effect of felbamate delivered intravenously in microparticles occurred at thirty minutes following administration, with an $ED_{50}$ of 27.2 mg/kg.

When an effective dosage was administered (50 mg/kg, intravenous), all mice tested were protected from seizures at thirty minutes. These results indicate that the microparticles delivered an effective amount of felbamate to the mice to alleviate seizures using intravenous administration.

The effect of microparticle/felbamate on minimal motor impairment (MMI) in mice following i.v. administration was also measured, at intervals of five minutes, fifteen minutes, thirty minutes, one hour and two hours, as shown in Table 2.

TABLE 2

The Effect of Microparticle/Felbamate on Minimal Motor Impairment in Mice Following I.V. Administration No. Toxic/No. Tested

| Dose (mg/kg) | 5 mins | 15 min. | 30 min. | 1 hr. | 2 hrs. |
|---|---|---|---|---|---|
| 100 | 1/8 | 0/8 | 0/8 | 0/8 | 1/8 |
| 125 | 2/8 | 0/8 | 0/8 | 1/8 | 0/8 |
| 150 | 2/8 | 1/8 | 1/8 | 1/8 | 0/8 |
| 175 | 2/8 | 3/8 | 5/8 | 4/8 | 1/8 |
| 200 | 5/8 | 14/16 | 16/16 | 12/16 | 8/16 |
| 250 | 7/7 | 7/7 | 7/7 | 7/7 | 6/7 |
| *0 | 0/5 | 0/5 | 0/5 | 0/5 | 0/5 |

*Microparticle alone: 644 mg/kg (equivalent material in the 200 mg/kg dose of microparticle/felbamate).

No mice were affected at any time when microparticles in vehicle not containing drug were used as control.

As shown below in Table 3, the $ED_{50}$ of intravenous felbamate microparticles was 27.2 mg/kg for protection against maximal electroshock seizures thirty minutes following administration, while the $ED_{50}$ for minimal motor impairment was found to be 167.3 mg/kg. The protective index (PI) was 6.15, which is determined by the ratio of the $ED_{50}$ for minimal motor impairment to the $ED_{50}$ for protection against maximal electroshock seizures (PI=$ED_{50}$ MMI/$ED_{50}$ MES=167.3 mg/kg/27.2 mg/kg=6.15).

Since felbamate is not soluble in aqueous media at clinically effective concentrations, an I.V. formulation does not exist. Thus, there is no clinically available I.V. formulation of felbamate for treating disorders such as status epilepticus and neuronal damage due to hypoxic/ischemic events.

Encapsulation of felbamate or similar compounds in microspheres and delivery by intravenous administration is an effective treatment for seizures that would be unavailable without prior microencapsulation in the diketopiperazine microparticles described herein.

TABLE 3

The Effect of Microparticle/Felbamate on Maximal Electroshock Seizures (MES) and Minimal Motor Impairment (MMI) in Mice Following I.V. Administration $ED_{50}$ (mg/kg)

| Test | 5 mins | 15 mins. | 30 min. | 1 hr | 2 hrs |
|---|---|---|---|---|---|
| MES | | 34.2<br>(24.2–43.7)<br>[6.5] | 27.2<br>(20.8–33.4)<br>[6.4] | 34.9<br>(26.6–43.1)<br>[7.7] | 47.3<br>(39.2–54.5)<br>[11.3] |
| MMI | 176.9<br>(150.4–220.4)<br>[6.2] | 176.6<br>(162.3–188.1)<br>[19.6] | 167.3<br>(155.0–177.2)<br>[28.1] | 174.1<br>(156.9–190.9)<br>[11.5] | 204.6<br>(189.5–229.1)<br>[15.3] |

95% Confidence interval given in parentheses
Slope given in brackets

Example 8

Pharmacokinetics of Salmon calcitonin (sCT) Encapsulated in Diketopiperazine Microparticles

Total[125] Radioactivity in Rat Plasma and Urine

Microparticles made from 2,5-diketo-3,6-di(4-fumarylaminobutyl)piperazine containing 1% sCT and $^{125}$I-sCT were administered at a dose of 10 μg/kg to rats (200–250 g) by oral gavage (n=6) and intravenous injection (n=7) via jugular vein cannula. The suspensions (10 and 100 mg/mL) were freshly made in 0.9% saline (pH 5.57) for injection. The volume of the suspension administered orally and intravenously was constant (0.2 mL) at both doses. Serial blood samples (100 μl) were withdrawn from the animals via jugular vein cannula. Following intravenous administration, blood was collected at five, fifteen, thirty, and forty five minutes, and one, two, four, six, ten and twelve hours. Blood was collected at similar times following oral administration beginning at fifteen minutes. Each blood sample was replaced with an equal volume of 0.9% saline and a trace amount of heparin to prevent blockage of the cannula. The total $^{125}$I radioactivity in plasma was determined using a scintillation counter.

FIG. 4*a* shows that the fraction (F) of total radioactivity absorbed (calculated by dividing the radioactivity absorbed by the total radioactivity administered) following oral administration of sCT/microparticle was 95%, compared with intravenous administration of unencapsulated sCT.

Determination of Plasma Salmon Calcitonin Levels in Canines by Radioimmunoassay Male, purebred beagles (eight per group) with a weight average of 12 kg received a single dose (10 μg/kg) of sCT in solution by subcutaneous and intravenous injection. In a crossover study one week later, 10 μg/kg of sCT in microparticles made from 2,5-diketo-3,6-di(4-fumarylaminobutyl)piperazine were administered to the same animals by oral gavage. The microparticle formulation containing 1% by weight sCT was administered as a suspension (10 mg/mL, total volume 1.2 mL) in 0.9% saline. The subcutaneous and intravenous formulation of sCT in solution was a solution of calcitonin (1 mg/mL, total volume 0.12 mL) in 0.9% saline. Blood (3 mL) was collected via direct vein puncture at 0 (pre-dose), five, fifteen, thirty, forty five, sixty, ninety, one hundred and twenty, one hundred and eighty, two hundred and forty, three hundred and sixty, and four hundred and eighty minutes and twenty four hours after administration. Changes in plasma calcium level (mg/dL) were monitored as described above and compared to a control of microparticles in saline. Plasma sCT concentrations (pg/mL) were determined by radioimmunoassay (Peninsula Laboratories, Inc., Belmont, Calif.).

FIGS. 4*b* and 4*c*, respectively, compare the plasma calcium and sCT concentration—time profiles zero to twenty four hours following oral administration of sCT in microparticles made from 2,5-diketo- 3,6-di(4-fumarylaminobutyl)piperazine and intravenous and subcutaneous administration of sCT in solution. The reduction in plasma calcium level observed following oral administration of sCT in microparticles is significant compared to administration of the microparticles alone and is similar to that following either intravenous or subcutaneous dosing. The plasma calcium levels for all three formulations fall at about the same rate. The maximal reduction in plasma calcium resulting from the oral dose is not as strong as that resulting from the subcutaneous and intravenous doses, but is sustained for a longer period of time.

The pharmacokinetic profiles of sCT in plasma are similar for the three dosage forms and exhibit rapid absorption and distribution of sCT. The maximal plasma sCT levels resulting from either sCT in microspheres administered orally or subcutaneous injection of sCT in solution occur within thirty minutes of administration. The sCT plasma level following the oral dose is maintained at a higher level and for a longer period of time (six to eight hours) than the levels obtained from the intravenous and subcutaneous injections.

Figure 4A:
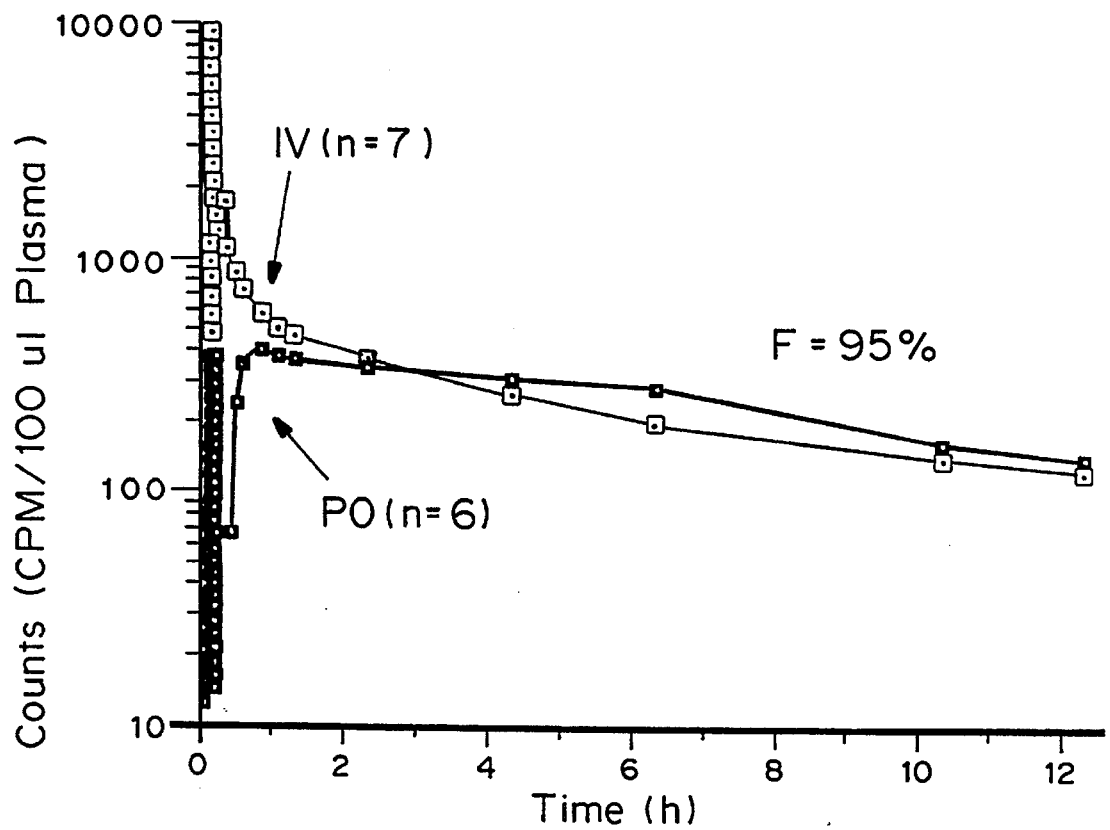
FIG. 4a is a graph of mean plasma total radioactivity counts (in CPM/100 µl plasma) versus time (hours) in rats following oral (PO) and intravenous (IV) administration of 10 µg/kg $^{125}$I-calcitonin ($^{125}$IsCT) loaded in microparticles made from 2,5-diketo-3,6-di(4-fumarylaminobutyl)piperazine. The fraction (F) represents the ratio of total radioactivity absorbed following oral administration of sCT/microparticle compared to intravenous injection of unencapsulated sCT. Dark squares represent oral administration. Light squares represent intravenous administration.
Figure 4B:
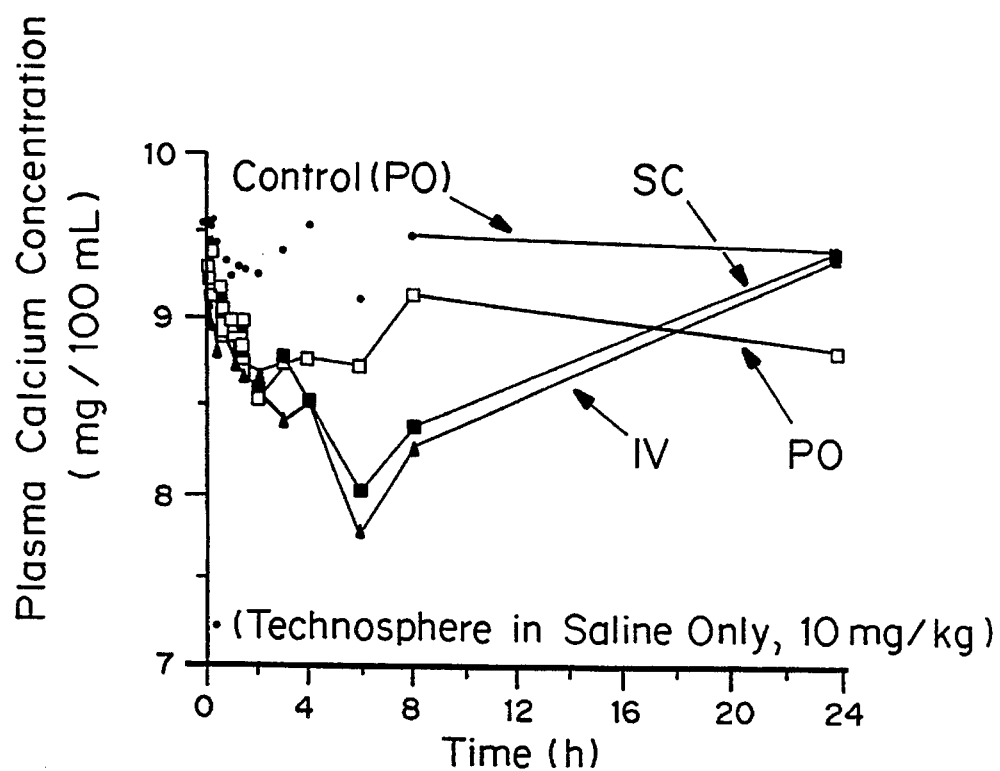
FIG. 4b is a graph comparing the plasma calcium concentration (in mg/dL) versus time (in hours) zero to twenty four hours following oral administration of salmon calcitonin (sCT) in microparticles made from 2,5-diketo-3,6-di(4-fumarylaminobutyl)piperazine and intravenous and subcutaneous administration of sCT in solution. Circles represent intravenous administration. Dark squares represent subcutaneous administration. Dot-filled squares represent oral administration.
Figure 4C:
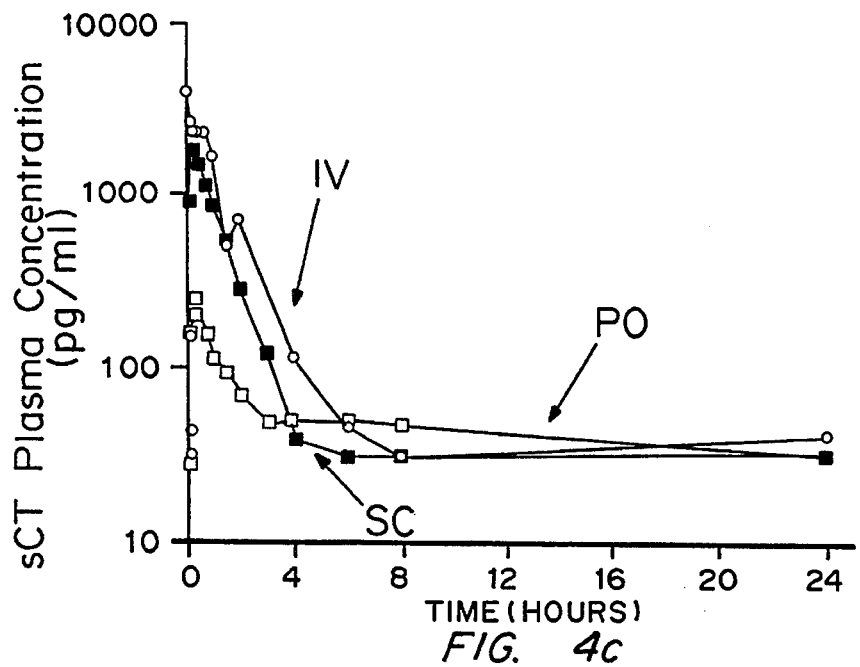
FIG. 4c is a graph of salmon calcitonin (sCT) concentration (in pg/mL) versus time (in hours) zero to twenty four hours following oral administration of sCT in microparticles made from 2,5-diketo- 3,6-di(4-fumarylaminobutyl)piperazine compared to intravenous and subcutaneous administration of sCT in solution. Circles represent intravenous administration. Dark squares represent subcutaneous administration. Dot-filled squares represent oral administration.
Figure 4D:
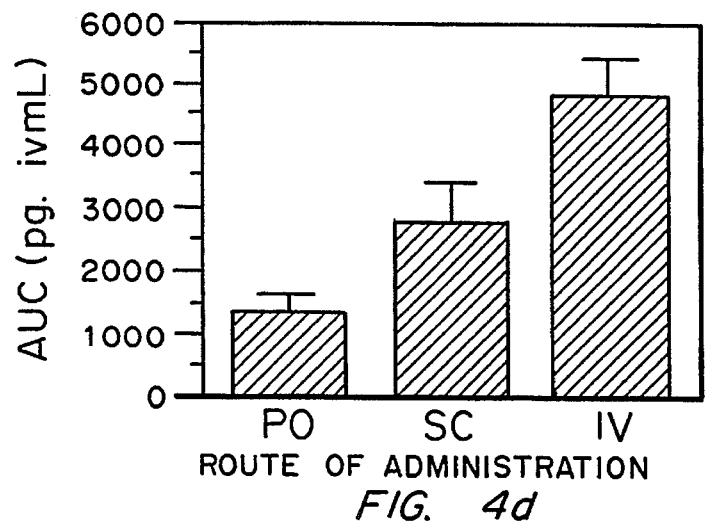
FIG. 4d is a graph of the mean area under the salmon calcitonin (sCT) plasma concentration-time curve (AUC) (in pg.h/mL) for oral sCT in microparticles made from 2,5-diketo-3,6-di(4-fumarylaminobutyl)piperazine (PO) compared to subcutaneous (SC) and intravenous (IV) injection of sCT in solution.
Figure 4E:
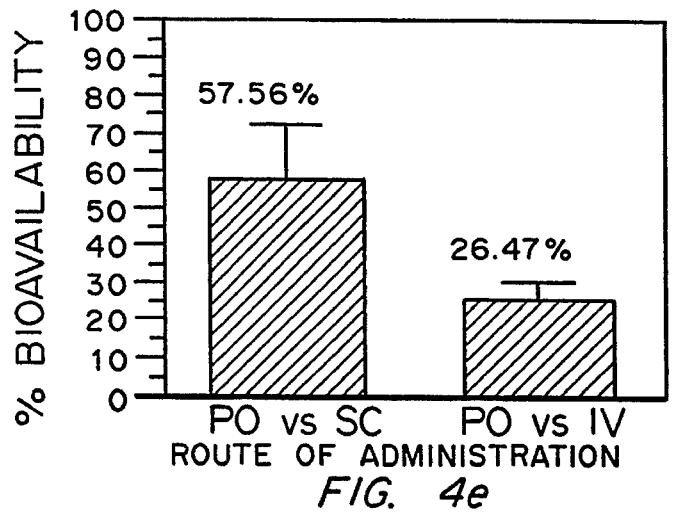
FIG. 4e is a graph comparing the percent bioavailability of oral sCT in microparticles made from 2,5-diketo-3,6-di(4-fumarylaminobutyl)piperazine to equivalent subcutaneous and intravenous doses of salmon calcitonin in solution.

FIGS. 4d and 4e show the mean area under the plasma sCT concentration—time curves (pg.h/mL) for oral sCT in microparticles made from 2,5-diketo-3,6-di(4-fumarylaminobutyl)piperazine (PO) and subcutaneous (SC) and intravenous (IV) injection of sCT in solution. The relative bioavailability of oral sCT in microparticles compared to an equivalent subcutaneous dose is 57.6%. The absolute bioavailability of orally administered sCT in microparticles compared to an equivalent intravenous dose is 26.5%.

Example 9

Acute Toxicology Studies Oral Administration

No toxic reactions to microparticles prepared from diketopiperazine derivatives, alone or containing calcitonin, haperin or insulin have been observed in rodents or canines. The following were monitored: diarrhea, vomiting, salivation, urination (excessive), heart rate, breathing, eyes (Prosis), nervousness/agitation, somnolence, state of the coat, swollen paws. Microparticles prepared from 2,5-diketo-3,6-di(4-succinylaminobutyl)piperazine were administered by oral gavage to rodents in doses up to 600 mg/kg and no changes were observed compared to a vehicle group. Microparticles prepared from 2,5-diketo- 3,6-di(4-succinylaminobutyl)piperazine containing heparin were administered by oral gavage to canines at doses up to 2.5 g/kg and no changes were observed compared to the vehicle control group.

Subcutaneous and Intravenous Administration

Microparticles made from 2,5-diketo-3,6-di(4-fumarylaminobutyl)piperazine in phosphate buffered saline were administered to rodents by intravenous injection at doses of 1, 5, 10, 15 and 38 mg/kg including a vehicle control of phosphate buffered saline (three animals per group). The rats in this experiment weighed between 125 and 148 g and the volume of the intravenous injection ranged from 0.07 to 0.30 mL. In a separate experiment microparticles made from 2,5-diketo-3,6-di(4-fumarylaminobutyl)piperazine in phosphate buffered saline were administered to rodents by subcutaneous injection at doses of 1, 5, 10 and 15 mg/kg including a vehicle control of phosphate buffered saline (three animals per group). The rats in this experiment weighed between 156 and 179 g and the volume of the intravenous injection ranged from 0.09 to 0.15 mL. The animals in both studies were monitored for twenty four hours after dosing at the following time-points: fifteen and thirty minutes, one, two, four, six and twenty four hours. Food and water was provided ad libidum. The following observations were made: physical condition (debilitation, dehydration, emaciation, abnormal breathing, comatose), behavior (placing response, startle response, writhing response), coat (unkempt, matting, alopecia), eyes (ptosis, discharge, opacity, dilation of pupils, inflammation of conjunctiva), nares and ears (discharge).

There were no detectable changes in the treated groups following the subcutaneous or intravenous administration of microparticles made from 2,5-diketo-3,6-di(4-fumarylaminobutyl)piperazine. These results indicate that absorption of large amounts of microparticles made from 2,5-diketo-3,6-di(4-fumarylaminobutyl)piperazine into the blood stream would produce no acute effects. Studies to assess the chronic effects of microparticle material have been completed at Hill Top Biolabs and are summarized below.

Example 10

Chronic Toxicology of Microparticles Administered Orally to Rodents

The following studies were performed at Hill Top Biolabs, Incorporated under FDA guidelines for preclinical toxicology studies.

A two week chronic toxicology study was carried out on the three groups of rodents of ten subjects each for two weeks. After fourteen days, the animals were sacrificed and checked for gross pathological changes. Blood was collected prior to the first dosing and at the time of sacrifice. The serum was removed afterspin down and a smack 20 analysis performed on each sample. A microscopic histopathological evaluation by a board-certified histopathologist was performed on the following tissues: heart, liver (2), lung, kidneys (2), esophagus, non-glandular stomach, glandular stomach, duodenum, jejunum, ileum, colon, rectum, mesenteric lymph node, bone marrow, and bone.

A dose of 50 mg/kg of microparticles made from 2,5-diketo-3,6-di(4-fumarylaminobutyl)piperazine (group 1) or microparticles containing 1% by weight of salmon calcitonin (group 2) was administered by oral gavage in a 20 mg/mL suspension in 0.1M citric acid and compared to 0.1M citric acid alone (group 3). The dose was repeated every twenty four hours for fourteen days and observations were made on the subjects. The animals were sacrificed at fourteen days.

A limit test was performed on two groups of rodents of ten subjects each by administering a single dose at day one and monitoring for two weeks following the dose. A dose of 5 g/kg of microparticles made from 2,5-diketo-3,6-di(4-fumarylaminobutyl)piperazine (group 4) was administered by oral gavage in a 0.25 g/mL suspension in 0.1M citric acid and compared to 0.1M citric acid alone (group 5). The animals were sacrificed at 14 days.

The results of this study are summarized below:
1. No mortalities occurred during the two week dosing period.
2. No gross pathological changes were observed in any of the subjects at the time of sacrifice.
3. Gastrointestinal tissues in all subjects were unremarkable.
4. No histomorphic changes were observed after treatment for fourteen days with the vehicle, microparticles, or microparticles containing 1% calcitonin.
5. No systemic toxicity was observed in any of the organs or tissues examined.
6. No significant difference was observed between the pre- and post-test blood chemistry analysis.
7. The $LD_{50}$ for microparticles was greater than 5.0 g/kg when given as a single dose.

8. The $LD_{50}$ for microparticles and 1% loaded microparticles/calcitonin was greater than 50 mg/kg when dosed daily for 14 days.

Modifications and variations of the compositions and methods of the present invention will be obvious to those skilled in the art from the foregoing detailed description. Such modifications and variations are intended to come within the scope of the appended claims.

We claim:

1. A microparticulate system for drug delivery comprising:

diketopiperazine microparticles, wherein the microparticles are stable at a first defined pH due to association and precipitation of the diketopiperazines and unstable at a second defined pH due to dissociation of the diketopiperazines, and wherein the diketopiperazine has the general structure

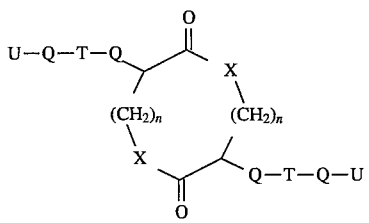

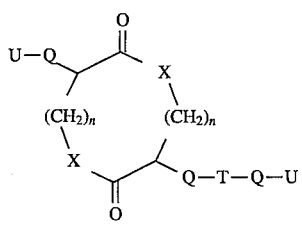

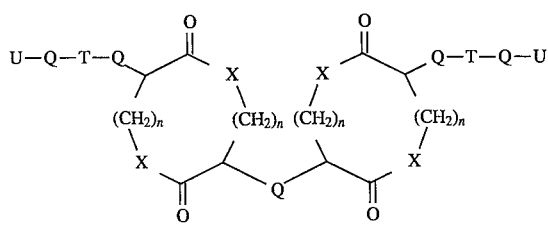

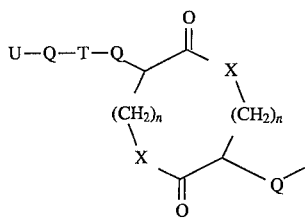

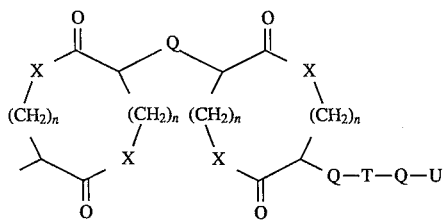

Wherein n is between 0 and 7, Q is, independently, a $C_{1-20}$ straight, branched or cyclic alkyl, aralkyl, alkaryl, alkenyl, alkynyl, heteroalkyl, heterocyclic, alkyl-heterocyclic, or heterocyclic-alkyl; T is —C(O)O, —OC(O), —C(O)NH, —NH, —NQ, —OQO, —O, —NHC(O), —OP(O), —P(O)O, —OP(O)$_2$, —P(O)$_2$O, —OS(O)$_2$, or —S(O)$_3$; U is an acid group, a basic group or a zwitterionic $C_{1-20}$ chain containing at least one acidic group and at least one basic group, wherein the side chains can be further functionalized with an alkene or alkyne group at any position, one or more of the carbons on the side chain can be replaced with an oxygen, one or more of the carbons can be functionalized with an acidic or basic group, and wherein the ring atoms X at positions 1 and 4 are either O or N.

2. The system of claim 1 wherein Q is selected from the group consisting of cis and trans —CH=CH—CO$_2$H, —CH(NHC(O)CF$_3$)—CH$_2$—CO$_2$H, —CH(NH$_2$)—CH$_2$—CO$_2$H, —CH(CH$_3$)=CH(CH$_3$)—CO$_2$H, —(CH$_2$)$_3$—CO$_2$H, —CH$_2$CH(CH$_3$)—CO$_2$H, —CH(CH$_2$CO$_2$H)=CH$_2$, -(tetrafluoro)benzoic acid, and -benzoic acid.

3. The system of claim 1 wherein the diketopiperazine is formed from amino acids selected from the group consisting of glutamic acid, aspartic acid, lysine, asparagine, ornithine and diaminopropionic acid.

4. The system of claim 3 wherein the structure is selected from the group consisting of 2,5-diketo-3,6-di(fumarylaminobutyl)piperazine, 2,5-diketo-3,6-di(glutarylaminobutyl)piperazine and 2,5-diketo-3,6-di(4-maleylaminobutyl)piperazine.

5. The system of claim 1 wherein the microparticles are stable at acidic pH and unstable at a more basic pH.

6. The system of claim 1 wherein the microparticles are unstable at acidic pH and stable at a more basic pH.

7. The system of claim 1 wherein the microparticles are stable at neutral pH and unstable at acidic and basic pH.

8. The microparticles of claim 1 further comprising a biologically active agent selected from the group consisting of proteins, peptides, polysaccharides, lipids, lipopolysaccharides, nucleic acids and other biologically active organic molecules.

9. The system of claim 8 wherein the biological agent is selected from the group consisting of insulin, calcitonin, felbamate, heparin, parathyroid hormone and fragments thereof, growth hormone, erythropoietin, AZT, DDI, G CSF, lamotrigine, chorionic gonadotropin releasing factor, luteinizing releasing hormone, β-galactosidase and Argatroban.

10. A method for making a microparticulate system for drug delivery comprising:

forming diketopiperazines in a solution with a first defined pH, adding a solution having a second defined pH, and precipitating the diketopiperazines to form microparticles, wherein the diketopiperazine has the general structure

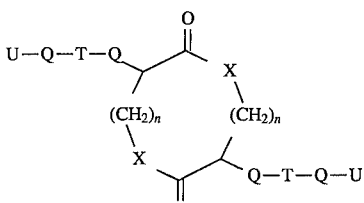

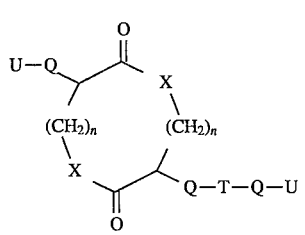

-continued

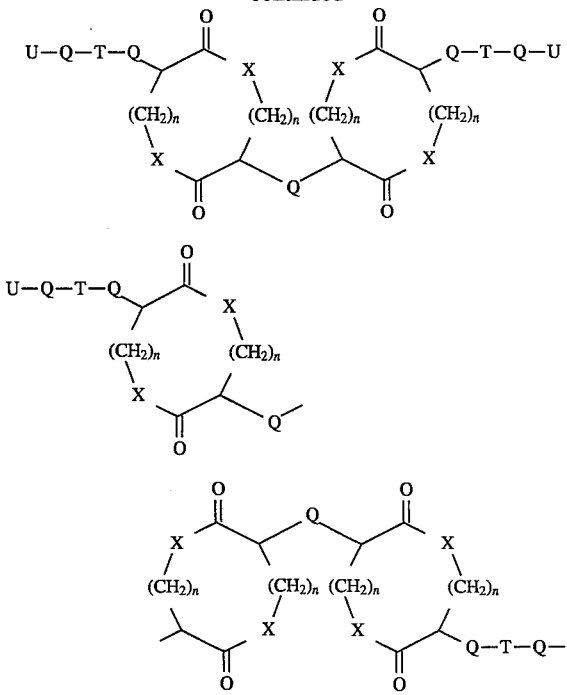

Wherein n is between 0 and 7, Q is, independently, a $C_{1-20}$ straight, branched or cyclic alkyl, aralkyl, alkaryl, alkenyl, alkynyl, heteroalkyl, heterocyclic, alkyl-heterocyclic, or heterocyclic-alkyl; T is —C(O)O, —OC(O), —C(O)NH, —NH, —NQ, —OQO, —O, —NHC(O), —OP(O), —P(O)O, —OP(O)$_2$, —P(O)$_2$O, —OS(O)$_2$, or —S(O)$_3$; U is an acid group, a basic group or a zwitterionic $C_{1-20}$ chain containing at least one acidic group and at least one basic group, wherein the side chains can be further functionalized with an alkene or alkyne group at any position, one or more of the carbons on the side chain can be replaced with an oxygen, one or more of the carbons can be functionalized with an acidic or basic group, and wherein the ring atoms X at positions 1 and 4 are either O or N.

11. The method of claim 10 wherein the diketopiperazine is formed from amino acids selected from the group consisting of glutamic acid, aspartic acid, lysine, ornithine and diaminopropionic acid, cyclized by (i) protecting side chain amino groups, (ii) heating the amino acids in a solvent to dimerize the amino acids, and (iii) removing the protecting groups.

12. The method of claim 11 further comprising acylating the ring nitrogens of the diketopiperazine.

13. The method of claim 9 wherein the structure is selected from the group consisting of 2,5-diketo-3,6-di(fumarylaminobutyl)piperazine, 2,5-diketo- 3,6-di(glutarylaminobutyl)piperazine and 2,5-diketo- 3,6-di(4-maleylaminobutyl)piperazine.

14. The method of claim 10 further comprising adding to the diketopiperazine solution a biologically active agent selected from the group consisting of proteins, peptides, polysaccharides, lipids, lipopolysaccharides, nucleic acids and other biologically active organic molecules, imaging agents, and cell specific targeting agents prior to forming the microparticles.

15. The method of claim 14 wherein the biological agent is selected from the group consisting of insulin, calcitonin, felbamate, heparin, parathyroid hormone and fragments thereof, growth hormone, erythropoietin, AZT, DDI, G CSF, lamotrigine, chorionic gonadotropin releasing factor, luteinizing releasing hormone, β-galactosidase and Argatroban.

16. The method of claim 10 further comprising coupling a targeting molecule to the diketopiperazine.

17. A method for administering a biologically active agent to a patient comprising providing the agent selected from the group consisting of proteins, peptides, polysaccharides, lipids, lipopolysaccharides, nucleic acids and other biologically active organic molecules, imaging agents, and cell specific targeting agents, in combination with microparticles formed of diketopiperazines, wherein the microparticles are stable at a first defined pH due to association and precipitation of the diketopiperazines and unstable at a second defined pH due to dissociation of the diketopiperazines.

18. The method of claim 17 wherein the microparticles further comprise compounds selected from the group consisting of stabilizers of the biologically active agents and non-encapsulated biologically active compounds.

19. The method of claim 17 wherein the microparticles are further encapsulated within an enteric coating.

20. The method of claim 17 wherein the microparticles are stable at acidic pH and unstable at a more basic pH.

21. The method of claim 17 wherein the microparticles are unstable at acidic pH and stable at a more basic pH.

22. The method of claim 17 wherein the microparticles are stable at neutral pH and unstable at acidic and basic pH.

23. The method of claim 10 wherein Q is selected from the group consisting of cis and trans —CH=CH—CO$_2$H, —CH(CH$_3$)=CH(CH$_3$)—CO$_2$H, —(CH$_2$)$_3$—CO$_2$H, —CH$_2$CH(CH$_3$)—CO$_2$H, —CH(CH$_2$CO$_2$H)=CH$_2$, -(tetrafluoro)benzoic acid and -benzoic acid.

24. The method of claim 10 wherein Q is selected from the group consisting of -aniline, -phenyl-C(NH)NH$_2$, -phenyl-C(NH)NH(alkyl), -phenyl-C(NH)N(alkyl)$_2$ and —(CH$_2$)$_4$NHC(O)CH(NH$_2$)CH(NH$_2$)CO$_2$H.

25. The method of claim 10 wherein Q is selected from the group consisting of —CH(NHC(O)CF$_3$)—CH$_2$—CO$_2$H, —CH(NH$_2$)—CH$_2$—CO$_2$H and —NH(CH$_2$)$_{1-20}$CO$_2$H.

26. The method of claim 17 wherein the biologically active agent is selected from the group consisting of hormones, anticoagulants, immunomodulating agents, cytotoxic agents, antibiotics, vasoactive agents, neuroactive agents, anaesthetics or sedatives, steroids, decongestants, antivirals, antisense, antigens, and antibodies.

27. The method of claim 17 wherein the biologically active agent is selected from the group consisting of insulin, calcitonin, felbamate, heparin, parathyroid hormone and fragments thereof, growth hormone, erythropoietin, AZT, DDI, G CSF, lamotrigine, chorionic gonadotropin releasing factor, luteinizing releasing hormone, β-galactosidase and Argatroban.

28. The method of claim 17 wherein the biologically active agent is not bioavailable when administered unencapsulated, and bioavailable when administered encapsulated, when administered to a patient via the same route of administration.

\* \* \* \* \*

UNITED STATES PATENT AND TRADEMARK OFFICE
CERTIFICATE OF CORRECTION

PATENT NO. : 5,503,852  Page 1 of 1
APPLICATION NO. : 08/299842
DATED : April 2, 1996
INVENTOR(S) : Solomon S. Steiner et al.

It is certified that error appears in the above-identified patent and that said Letters Patent is hereby corrected as shown below:

Claim 13, Line 1:

Please delete the words "claim 9" and insert the words -- claim 10 -- in place thereof.

Signed and Sealed this

Seventeenth Day of April, 2007

JON W. DUDAS
*Director of the United States Patent and Trademark Office*